United States Patent [19]
Olovson

[11] Patent Number: 5,032,114
[45] Date of Patent: Jul. 16, 1991

[54] SYRINGE

[76] Inventor: Gudmar Olovson, 64, rue Saint-Charles, 75015 Paris, France

[21] Appl. No.: 488,020
[22] PCT Filed: Nov. 22, 1988
[86] PCT No.: PCT/SE88/00634
§ 371 Date: May 16, 1990
§ 102(e) Date: May 16, 1990
[87] PCT Pub. No.: WO89/04677
PCT Pub. Date: Jun. 1, 1989

[30] Foreign Application Priority Data
Nov. 25, 1987 [SE] Sweden .............................. 8704688
Jan. 14, 1988 [SE] Sweden .............................. 8800098

[51] Int. Cl.⁵ .............................................. A61M 5/00
[52] U.S. Cl. .................................... 604/110; 604/228
[58] Field of Search ............... 604/110, 187, 218, 228, 604/208, 211

[56] References Cited
U.S. PATENT DOCUMENTS 4,391,272  7/1983  Staempfli .
4,699,614  10/1987  Glazier .
4,861,338  8/1989  Mathiesen et al. ................ 604/110
4,906,231  3/1990  Young ................................ 604/110
4,908,020  5/1990  Pettersen ...................... 604/228 X
4,950,243  8/1990  Estruch ............................ 604/110

FOREIGN PATENT DOCUMENTS
0229017  7/1987  European Pat. Off. .
438598  4/1985  Sweden .

Primary Examiner—John D. Yasko
Attorney, Agent, or Firm—Burns, Doane, Swecker & Mathis

[57] ABSTRACT

The invention relates to a syringe (1) comprising a container (2), a needle (3) capable of co-acting with one end of the container, a plunger (4) which is arranged in the container and which sealingly co-acts with the inner surface (2c) thereof, and a rod-shaped element (5) which co-acts with the plunger (4) and which is arranged for reciprocating movement relative to the container (2), such that movement of the element from the one end (2a) in a first direction (P1) enables the container (2) to be filled with injection liquid, while linear movement in the opposite direction (P2) causes liquid in the container to be discharged therefrom through the needle (3). Provided between the plunger (4) and the element (5), for their mutual co-action, is a crewsthreaded means (6) which holds the plunger (4) firmly to the rod-shaped element (5) when the element moves in the first direction (P1) but which adopts an inactive state when the element (5) is moved in the opposite direction, therewith rendering refilling of the container impossible.

14 Claims, 2 Drawing Sheets

SYRINGE

TECHNICAL FIELD

The present invention relates to a syringe, and more particularly but not exclusively, to a hand-operated syringe of the kind which comprises a container, a needle which cooperates with one end of the container, a plunger which is located inside the container and which co-acts sealingly with the inner surface thereof, and a rod-shaped element which co-acts with the plunger for reciprocating plunger movement in said container. The rod-shaped element is capable of being displaced rectilinearly relative to the container, such that linear movement of said element in a first direction from said one end causes the container to be filled with liquid to be injected, while linear movement of the element in a second direction causes the liquid to be emptied from the container through the needle.

The present invention is concerned primarily with a disposable-type syringe, by which is meant a syringe whose container can be filled with injection liquid only once, i.e. after being once filled it can never be filled again.

BACKGROUND PRIOR ART

Several variants of syringes of this kind are known to the art.

In a first variant of these known syringes the mutual co-action of the plunger and the rod-shaped element is facilitated with the aid of means located between said plunger and said element, this means holding the plunger to the rod-shaped element during linear movement of the element in said first direction and also during linear movement of the element in said second direction. Thus, there is no detachable connection between the plunger and the rod-like element and the plunger will thus be moved backwards and forwards in the container in precise response to the direction of movement of the rod-shaped element.

This means that the container can be filled with liquid each time the plunger is moved away from the needle, and emptied of liquid each time the plunger is moved towards the needle, thereby enabling the syringe to be used over and over again.

The repeated use of one and the same syringe has proven to constitute a serious risk of spreading disease, such as AIDS.

Consequently, single-shot syringes have been proposed, which can be used only once for injection purposes, after which the container can no longer be filled.

An example of such single-shot syringes is described and illustrated in European Patent Application Ser. No. 0 229 017, in which syringe the plunger and rod-shaped element co-act with one another through the intermediary of hook-shaped members which are moved out of engagement with the plunger upon movement of the rod-shaped element towards the needle.

The Swedish Patent Specification Publ. No. 413 838 describes and illustrates a so-called single-shot syringe in which the rod-shaped element incorporates a weakening at a location adjacent the plunger, and in which means are provided for twisting the element relative the plunger subsequent to completing an injection, thereby fracturing the rod-shaped element at the weakened location.

The Swedish Patent Specification Publ. No. 438 598 also teaches a single-shot, or disposable, syringe.

SUMMARY OF THE INVENTION

TECHNICAL PROBLEMS

When viewing the earlier prior art it will be seen that a technical problem is one of providing a syringe which can be filled with injection liquid in a conventional manner and in which when the plunger is moved towards the needle there is activated a means which renders it impossible to refill the container with liquid, since the ability of the syringe to draw in liquid by suction is placed out of function, irrespective of how careful the plunger is moved towards the needle.

It must also be considered a qualified technical problem to provide a disposable, or single-shot hypodermic syringe which is so constructed as to render it impossible to use the syringe more than once, even though conscious efforts are made to do so.

Another qualified technical problem resides in the realization that a syringe which is to resolve the aforesaid technical problems should be provided between the plunger and the rod-shaped element with attachment means of very special qualities.

It will also be seen that a further technical problem is one of realizing that there should be provided between the rod-shaped element and the plunger a means which will guarantee positive co-action between the rod-shaped element and the plunger when the plunger is moved for the first time from its lowermost position to its maximum extended position, in order to fill the container with injection liquid, and that this means shall be brought to a state in which said co-action is non-existant subsequent to careful displacement of the plunger towards the needle through a short distance.

Another qualified technical problem in this regard is one of enabling the container to be given a cross-sectional shape which deviates slightly from a circular line, such as to prevent rotation of the plunger in the container.

It will also be seen that a technical problem resides in the provision of conditions, with the aid of simple means, which enable the rod-shaped element to be guidingly rotated about its longitudinal axis in response to linear displacement of said element, and therewith adapt rotation of the element in relation to the plunger so that when the plunger, irrespective of its position in the container (with the exception of a very small distance from the bottom) is moved towards the needle in order to inject liquid, the co-action between the rod-shaped element and the plunger is discontinued in a manner such as to render re-filling of injection liquid impossible.

SOLUTION

While taking into consideration the earlier prior art and with consideration to the aforesaid technical problems, the present invention relates to a syringe which comprises a container, a needle which cooperates with one end of the container, a plunger which is located inside the container and which sealingly co-acts with the inner surface thereof, and a rod-shaped element which co-acts with the plunger and which is arranged for linear movement relative to the container such that linear movement of said element in a first direction from said one end causes the container to be filled with liquid to be injected, while linear movement of the element in a second direction opposite to said first direction causes the liquid to be emptied from the container through the needle.

The invention is based on a syringe of this kind in which there is provided between the plunger and the rod-shaped element a means which holds the plunger firmly to the rod-shaped element when the element is moved linearly in said first direction.

The invention is also based on a disposable, or single-shot, syringe of the kind in which upon displacement of the rod-shaped element and the plunger in the opposite direction the aforesaid means is brought to an inactive position in which it discontinues the co-action between said element and the plunger, such that no injection liquid will be drawn into the container upon further linear movement of said element in the first direction.

In accordance with the present invention the aforesaid means in such disposable syringes is capable of being rotated relative to the plunger as a result of said linear movement, and the rod-shaped element and plunger of said syringe co-act with one another via a screw thread.

In accordance with one embodiment of the invention the plunger is provided with a screwthreaded hole and the rod-shaped element presents a correspondingly screwthreaded part. As will be understood, the location of the screw-threaded hole and the screwthreaded part may be reversed.

The container preferably has a cross-sectional shape which deviates from a circular line (an eliptical shape), thereby to prevent corotation of the plunger when the rod-shaped element is caused to rotate about its longitudinal axis during linear displacement of said element.

The rod-shaped element has a helical configuration of large pitch, such that when the element is moved linearly through a pre-determined short distance it will rotate to such an extent as to unscrew the plunger from said element thereby discontinuing the mutual co-action therebetween.

In order to impart to the rod-shaped element a rotary movement which cannot be perceived by the personnel it is proposed in accordance with the invention that a non-rotatably attached plate, or thrust plate, is arranged to co-act with the rod-shaped element from the end facing the plunger.

Finally, it is proposed that when co-action between the plunger and the rod-shaped element is discontinued a catch means is inserted in order to prevent renewed co-action between said element and the plunger.

ADVANTAGES

The advantages primarily afforded by a syringe according to the present invention reside in the possibility of providing, in a simple fashion, a disposable syringe with which the syringe container can be filled with injection liquid only once, and with which the container can be emptied, or partially emptied, of liquid only once, and with which the ability of the container to take in liquid is placed out of function, even if measures are taken to prevent this from happening, thereby rendering refilling of the container impossible.

The primary characteristic features of a syringe constructed in accordance with the present invention are set forth in the characterizing clause of the following claim 1.

BRIEF DESCRIPTION OF THE DRAWINGS

Some preferred embodiments of a syringe constructed in accordance with the present invention will now been described in more detail with reference to the accompanying drawings, in which.

DESCRIPTION OF PREFERRED EMBODIMENTS

Figure 1:
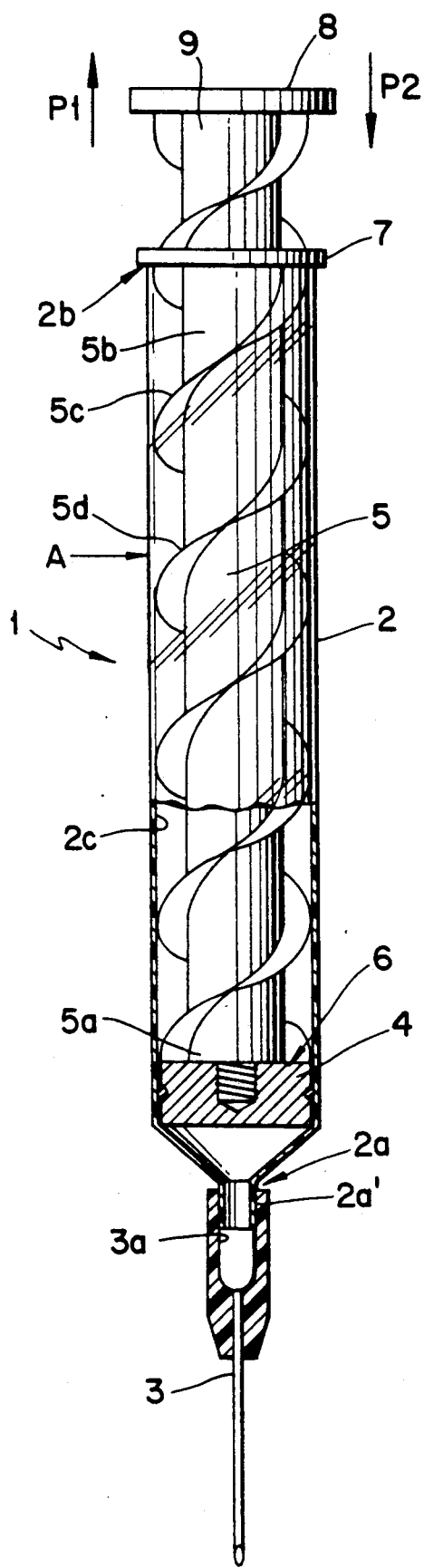
FIG. 1 is a partially sectioned side view of a syringe showing a means significant of the invention and acting between a plunger and a road-shaped element in an active position.

In FIG. 1 there is illustrated a syringe 1, a hypodermic syringe, which comprises a container 2 having a needle 3 which cooperates with one end 2a of the container and which is provided with an inner, conical socket-like member 3a intended to embrace an outer conical peg 2a' in a known manner.

The syringe illustrated in FIG. 1 also includes a plunger 4, which in the illustrated embodiment is shown fully depressed in the container 2 and which is intended to co-act sealingly with the inner surface 2c of the container 2. Co-acting with the plunger 4 is a rod-shaped element 5 which can be displaced linearly by hand in relation to the container 2 such as to move the element in a first direction "P1" away from said one end 2a, therewith to fill the container 2 with injection liquid, and in a second direction "P2" towards said one end 2a, therewith to eject the liquid in the container through the needle 3, there being provided between the plunger 4 and the element 5, at the end 5a of said element, a means 6 which is operative in providing this particular co-action between said plunger and said element and which holds the plunger 4 firmly to the element 5 during movement in the first direction "P1". During this first movement, the container 2 is filled with liquid as a result of the partial vacuum prevailing in the container.

Figure 2:
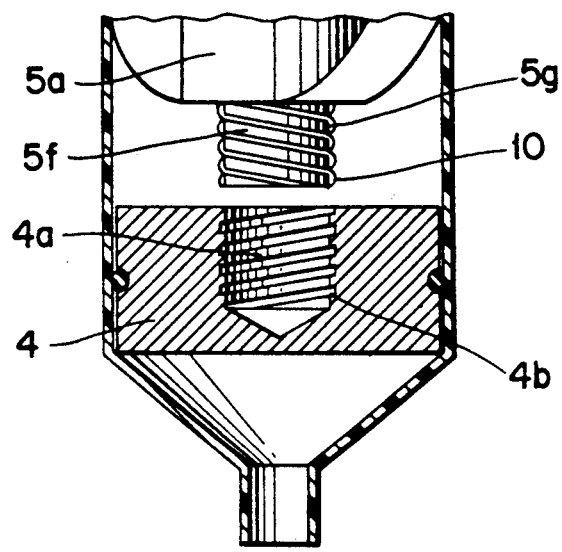
FIG. 2 is a side view in larger scale of the aforesaid means in an inactive position.

In accordance with the invention, the means 6 is brought to an inactive position, shown in FIG. 2, when the rod-shaped element 5 and the plunger 4 are moved a short distance in the opposite direction "P2", such as to discontinue the mutual co-action between the element 5 and the plunger 4. As a result hereof no injection liquid will be drawn into the container 2 when the rod-shaped element 5 is again moved in the first linear direction "P1", since the plunger 4 is unable to accompany the element 5.

According to the present invention this inactive position of the means 6 is obtained immediately the plunger 4 and the element 5 are stopped and urged slightly in the opposite direction. This can thus be caused to take place when the part 5a of the element 5 is located in a position referenced "A" in FIG. 1.

With regard to the element 5, said element when moved in the direction "P1" will rotate the plunger 4 in the direction of a right-hand screwthread. The element 5 and the plunger 4 co-act with one another through the intermediary of a screwthread (left-hand screwthread).

This rotational movement of the element 5 is achieved through the particular construction of said element. Thus, the element 5 comprises an inner rod 5b having provided thereon two right-hand helical lands 5c which form a screwthread having two leads or threads having a large pitch.

Figure 4:
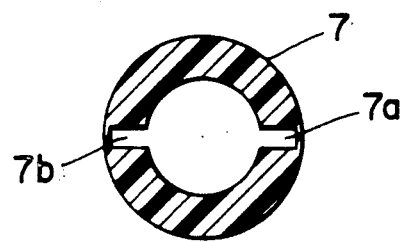
FIG. 4 is a cross sectional view of an upper container cover plate which is intended to rotate the rod-shaped element about its longitudinal axis in response to linear movement of said element.

It will be seen from FIG. 4 that the land or projection 5c is intended to co-act with a recess or cut-out 7a in an upper container cover-plate 7, whereas the land or projection 5d is intended to co-act with a recess or cut-out 7b. The syringe also includes an upper plate 8 which is rotatable connected to the element 5 through the intermediary of a rotational shaft 9 in a known manner.

The advantage with this embodiment is that the lands 5c and 5d need not connect with the inner surface of the container, but can be made narrower.

As will be seen from FIG. 2, the plunger 4 is provided with a screwthreaded hole 4a provided with a screwthread 4b, and that the end 5a of the rod-shaped element 5 has a peg 5f which is provided with a corresponding screwthread 5g.

Figure 3:
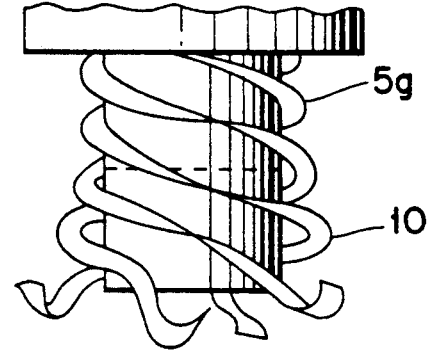
FIG. 3 illustrates one embodiment of a catch means in larger scale than that of FIG. 2.

The screwthreads 4b and 5a are left-hand screwthreads and in practice the pitch of the threads is much larger than that shown in FIGS. 2 and 3.

In the case of the illustrated embodiment, linear movement of the element 5 in the direction of the arrow "P1" will result in counter clockwise rotation of the element 5 whereas the left-hand screwthread of the plunger 4 ensures that the plunger is held to the lower part 5a of the element 5.

As soon as this movement stops and the element is moved linearly in the direction of arrow "P2", the plunger 4 will be unscrewed from the element 5. This discontinuation of the co-action between said plunger and said element takes place after only a short distance. As will be understood, the plunger 4 may not rotate together with the element 5. Consequently, the container may be given a slightly eliptical cross-sectional shape.

As an alternative embodiment, the rotational movement imparted to the element 5 during its linear movement from the position shown in FIG. 1 to a position in which the part 5a is located in the position referenced "A" is sufficient for a left-hand screwthread 5g on the peg 5a to be moved out of co-action with the thread 4b in the recess 4a.

The screwthreads 5g and 4b may have or threads and different pitches in both cases.

It is a prerequisite of the function of the invention that linear movement of the element 5 will positively result in rotational movement relative to the element 5 and the plunger 4, and consequently it is suggested in accordance with the invention that the container 2 is given a cross-sectional shape which deviates from a circular line, and that the plunger 4 is optionally given a shape adapted thereto, thereby making it more difficult to rotate the plunger 4 relative to the container 2 than the element 5.

The extent to which the cross-sectional shape of the container shall deviate from a circular line depends upon the material from which the plunger 4 is made and on how readily the screwthread 5g co-acts with the screwthread 4b.

As beforementioned, a plate or cover 7 co-acts with the other end 2b of the container 2. This cover plate is welded to the container 2, or secured thereto in some other known manner, and presents grooves or slots 7a, 7b by means of which the element 5 is caused to rotate about its longitudinal axis to an extent corresponding to the linear movement of said element. This cover plate is affixed to the container subsequent to the element 5 and the plunger 4 being inserted into the container 2 in their mutually co-acting state.

In accordance with the invention, when the mutual co-action between the plunger 4 and the element 5 is discontinued, as shown in FIG. 2, a catch means 10 may be inserted between the screwthreads, thereby preventing the screwthread 5g from being re-screwed into the screwthread 4b. The catch means 10 is shown in FIG. 3 and comprises a helical wire which is screwed to the lower part of the screwthread 5g and which in a freed position forms a stop against co-action between the screwthreads 5g and 4b.

The catch wire 10 may have the form of a screwthread so that it is able to co-act with the screwthread 4b and, when co-action is discontinued, to take a helical form around the peg 5f, thereby making renewed co-action between the screwthreads 5g and 4b impossible.

Other embodiments of such catch means are conceivable.

All of the syringe components, possibly with the exception of the plunger 4, are preferably manufacture from a suitable plastics material.

It is also proposed that the pitch of the screwthreads 5c and 5d is adapted to the pitch of the screwthreads 5g and 4b, so that the plunger 4 will discontinue its co-action with the rod-shaped element 5 when the element is moved linearly through a distance of less than 50% of the possible maximum distance, preferably less than 25% of said maximum distance.

The shorter the linear distance moved, the better the technical advance.

It is to be noted that a distance must be arranged between the outer part or surface of the land 5d and the inner surface of the container 2.

Further the plate or cover 7 shall coacts with the upper end 2b of the container by welding or other similar means.

Figure 5:
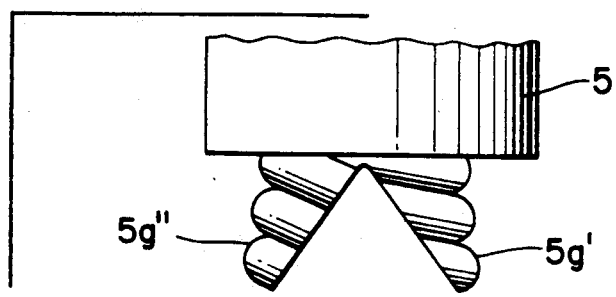
FIG. 5 illustrates a second embodiment of a catch means and a recess in the plunger.

In FIG. 5 illustrates a second embodiment of a catch means and a recess in the plunger 4. In this embodiment the screwthread has the form of two diverging legs 5g' och 5g". When these legs are pressed together they match the thread in the recess 4a and thus in an active position they cooperate with eachother. When the element 5 is pressed downwards the plunger 4 and the legs will be moved to inactive position and than the legs will bend to the position shown.

In FIG. 5 it is illustrated that threads are arranged along the legs 5g' och 5g" and these legs, when leaving the recess 4a and the threads 4b, are diverging in such an extent that they can not more cooperate with the threads 4b.

Figure 6:
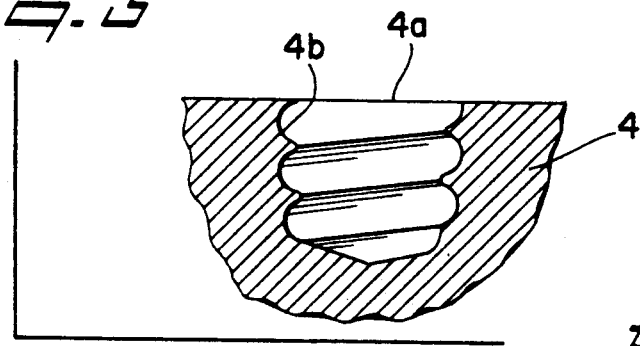
FIG. 6 illustrates a third embodiment of a catch means.
Figure 6:
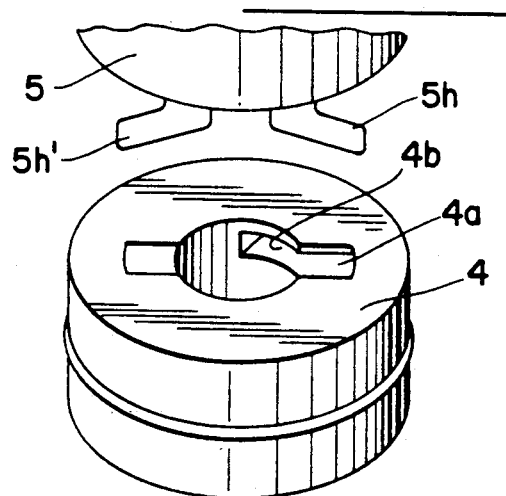

In the embodiment shown in FIG. 6 the legs are formed as protrudings 5h and 5h' intended to cooperate with the recess 4a and the threads 4b in the plunger 4. The function here is identical to the one shown in FIG. 5.

Figure 7:
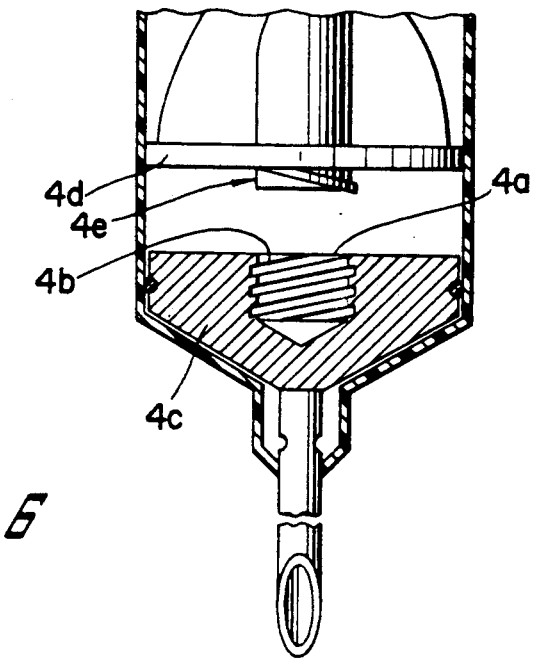
FIG. 7 illustrates a two-part plunger arrangement and with the two parts arranged at a distance from eachother and FIG. 8 illustrates a horisontal view of the upper part of the plunger shown in FIG. 7

FIG. 7 illustrates a two-part plunger arrangement and showing the two parts at a distance from eachother.

One part 4c has a recess 4a and a thread 4b and the other part 4d has a threaded portion 4e intended to cooperate with eachother as previously described.

The turning of 180° is sufficient to cause the two parts to move from active to inactive position. The threaded portion 4e may have a construction as illustrated in FIGS. 3,5,6 or 9.

Figure 8:
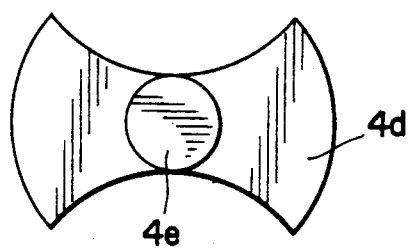

FIG. 8 illustrates a horisontal view of the upper part of the plunger shown in FIG. 7.

Figure 9:
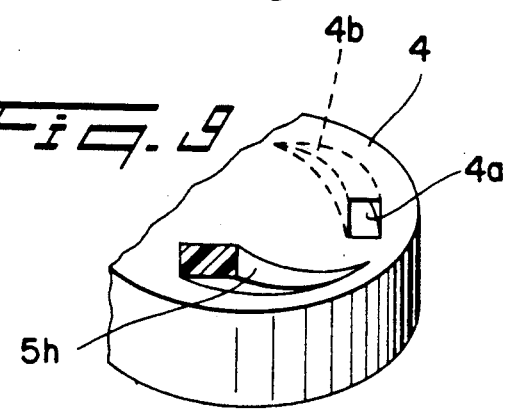
FIG. 9 illustrates a further embodiment of a catch means.

In the embodiment shown in FIG. 9 it has been illustrated that the protruding 5h has the form of pointed portion intended to cooperate with the recess 4a and the thread 4b, where said thread has the form of a slooping recess. The function of this embodiment is identical to the one described in FIG. 5.

Each of the illustrated embodiments exposes the feature that after the parts 5g', 5g" have been in cooperation with the recess 4a and the threads 4b these parts are moved to another position in which no previously established cooperation is possible.

It will be understood that the invention is not restricted to the aforedescribed embodiments, and that modifications can be made within the scope of the following claims.

I claim:

1. A syringe comprising a container, a needle capable of co-acting with one end of the container, a plunger which is located inside the container and which co-acts sealingly with the inner surface thereof, and a rod-shaped element which co-acts with the plunger and which is arranged for rectilinear reciprocating movement relative to the container, such that linear movement of said element in a first direction from said one end causes the container to be filled with liquid to be injected, while linear movement of the element in a second direction causes the liquid to be emptied from the container through the needle, there being provided between the piston and the rod-shaped element, for their mutual co-action, a means which during linear movement of said element in said first direction holds the plunger against the rod-shaped element and which upon linear movement of the element and the plunger in the opposite direction takes an inactive state in which co-action between the rod-shaped element and the plunger is discontinued, therewith to prevent further liquid from being drawn into the container upon renewed linear movement of the rod-shaped element in the first direction, characterized in that means are provided for imparting rotational movement to the rod-shaped element relative to the plunger upon linear movement of said element; and in that the rod-shaped element and the plunger mutually co-act through the intermediary of a screwthread.

2. A syringe according to claim 1, characterized in that the plunger is provided with a screwthreaded hole, and in that the rod-shaped element is provided with a correspondingly screwthreaded peg.

3. A syringe according to claim 1, characterized in that the container has a cross-sectional shape which deviates from a circular line.

4. A syringe according to claim 1, characterized in that the other end of the container co-acts with a cover means provided with a groove by means of which the rod-shaped element is rotated to an extent corresponding to the distance through which said element is moved linearly.

5. A syringe according to claim 4, characterized in that the rod-shaped element has a helical configuration.

6. A syringe according to claim 5, characterized in that the end of the rod-shaped element remote from the plunger co-acts with a plate rotatably mounted on the element.

7. A syringe according to claim 1, characterized by a catch means insertable between the plunger and the rod-shaped element upon discontinuation of the mutual co-action therebetween such as to prevent this co-action from being re-established.

8. A syringe according to claim 1, characterized by a catch means in the form of two dirverging legs.

9. A syringe according to claim 1, characterized by a plunger arrangement in which the plunger is in the form of two parts separated from eachother by the turning of one part relative the other less than 360° preferably about 180°.

10. A syringe according to claim 2, characterized in that the container has a cross-sectional shape which deviates from a circular line.

11. A syringe according to claim 2, characterized in that the other end of the container co-acts with a cover means provided with a groove by means of which the rod-shaped element is rotated to an extent corresponding to the distance through which said element is moved linearly.

12. A syringe according to claim 3, characterized in that the other end of the container co-acts with a cover means provided with a groove by means of which the rod-shaped element is rotated to an extent corresponding to the distance through which said element is moved linearly.

13. A syringe according to claim 10, characterized in that the other end of the container co-acts with a cover means provided with a groove by means of which the rod-shaped element is rotated to an extent corresponding to the distance through which said element is moved linearly.

14. A syringe according to claim 2, characterized by a catch means insertable between the plunger and the rod-shaped element upon discontinuation of the mutual co-action there between such as to prevent this co-action from being reestablished.

* * * * *